United States Patent
Wu et al.

(10) Patent No.: US 11,866,756 B2
(45) Date of Patent: Jan. 9, 2024

(54) METHODS FOR CO-PRODUCING ERYTHRITOL AND ARABINOSE BY USING XYLOSE MOTHER LIQUOR

(71) Applicant: ZHEJIANG HUAKANG PHARMACEUTICAL CO., LTD., Zhejiang (CN)

(72) Inventors: Aijuan Wu, Quzhou (CN); Jiaxing Luo, Quzhou (CN); Changhui Hu, Quzhou (CN); Mingqian Yang, Quzhou (CN); Chengjun Liao, Quzhou (CN); Yi Zheng, Quzhou (CN); Shuncheng Fang, Quzhou (CN); Mian Li, Quzhou (CN)

(73) Assignee: ZHEJIANG HUAKANG PHARMACEUTICAL CO., LTD., Quzhou (CN)

( * ) Notice: Subject to any disclaimer, the term of this patent is extended or adjusted under 35 U.S.C. 154(b) by 0 days.

(21) Appl. No.: 18/354,044

(22) Filed: Jul. 18, 2023

(65) Prior Publication Data
US 2023/0357805 A1  Nov. 9, 2023

Related U.S. Application Data

(63) Continuation of application No. PCT/CN2022/133112, filed on Nov. 21, 2022.

(30) Foreign Application Priority Data

Dec. 26, 2021  (CN) .......................... 202111606216.9

(51) Int. Cl.
| | |
|---|---|
| C13K 13/00 | (2006.01) |
| C12N 1/16 | (2006.01) |
| C07C 31/12 | (2006.01) |
| C12P 7/04 | (2006.01) |
| C12P 7/02 | (2006.01) |
| C10L 1/02 | (2006.01) |
| C12P 19/02 | (2006.01) |
| C12P 7/18 | (2006.01) |
| C12R 1/85 | (2006.01) |

(52) U.S. Cl.
CPC ................ C12P 7/18 (2013.01); C12N 1/165 (2021.05); C12P 19/02 (2013.01); *C12R 2001/85* (2021.05)

(58) Field of Classification Search
CPC ...... C12M 47/02; C13K 13/002; C12N 1/165; C12P 7/04; C12P 7/02; C12P 19/02; C10L 1/02; C07C 31/12
See application file for complete search history.

(56) References Cited

U.S. PATENT DOCUMENTS 5,902,739 A   5/1999  Abe et al.

FOREIGN PATENT DOCUMENTS

| CN | 101372700 A | 2/2009 |
|---|---|---|
| CN | 101502308 A | 8/2009 |
| CN | 101555503 A | 10/2009 |
| CN | 101643752 A | 2/2010 |
| CN | 101921810 A | 12/2010 |
| CN | 101705253 B | 3/2012 |
| CN | 102850408 A | 1/2013 |
| CN | 101857523 B | 4/2013 |
| CN | 104011215 A | 8/2014 |
| CN | 102603814 B | 1/2015 |
| CN | 102952165 B | 1/2016 |
| CN | 109504733 A | 3/2019 |
| CN | 111363759 A | 7/2020 |
| CN | 112094956 A | 12/2020 |
| CN | 114181268 A | 3/2022 |
| JP | H09154590 A | 6/1997 |

OTHER PUBLICATIONS

International Search Report in PCT/CN2022/133112 dated Jan. 17, 2023, 7 pages.
Written Opinion in PCT/CN2022/133112 dated Jan. 17, 2023, 9 pages.

*Primary Examiner* — Maryam Monshipouri
(74) *Attorney, Agent, or Firm* — METIS IP LLC

(57) ABSTRACT

The embodiments of the present disclosure provides a method of co-producing erythritol and arabinose by using a xylose mother liquor, wherein an extract and a raffinate are obtained by separating the xylose mother liquor through a first chromatography, the extract is configured to prepare crystallized xylose, the raffinate and the liquid glucose or crystallized glucose are blended and erythritol is produced by using a *Yarrowia lipolytica* with high osmotolerant and a high conversion rate. erythritol crystals are obtained by centrifugation and crystallization first by using characteristics of low solubility degree and easy crystallization of the erythritol, the arabinose raffinate having a high content of arabinose is obtained by separating a centrifuged erythritol mother liquor through a second chromatography, and arabinose crystals are obtained based on the arabinose raffinate.

6 Claims, 1 Drawing Sheet

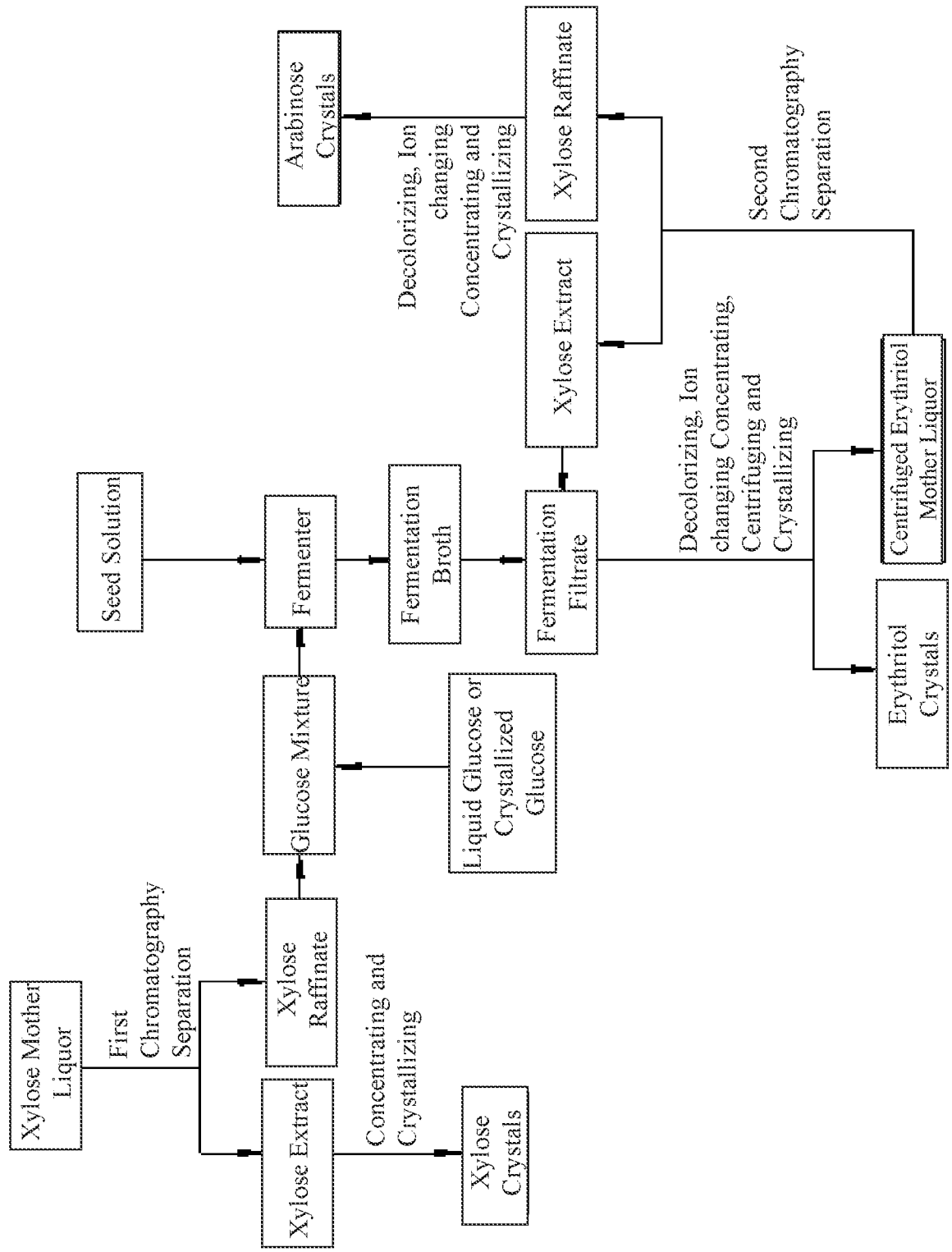

METHODS FOR CO-PRODUCING ERYTHRITOL AND ARABINOSE BY USING XYLOSE MOTHER LIQUOR

CROSS-REFERENCE TO RELATED APPLICATIONS

This application is a continuation of International Application No. PCT/CN2022/133112 filed on Nov. 21, 2022, which claims priority to Chinese Patent Application No. 202111606216.9 filed on Dec. 26, 2021, the entire contents of which are incorporated herein by reference.

TECHNICAL FIELD

The present disclosure relates to the technical field of xylose mother liquor utilization, and in particular to methods for co-producing erythritol and arabinose by utilizing xylose mother liquor.

BACKGROUND

A xylose mother liquor usually refers to a waste sugar liquid left after a production of xylose/xylitol using a chemical process. The xylose content of the xylose mother liquor is between 40% W/V~60% W/V, 10% W/V~20% W/V of glucose, 15% W/V~20% W/V of arabinose, 0~10% W/V of mannose and 0~5% W/V of galactose. The xylose mother liquor has a high content of hetero sugar and is often sold as a by-product for making caramel pigments, etc., an added value of which is low. A comprehensive utilization of the xylose mother liquor is a key concern in the field of xylose/xylitol industry.

At present, a research on methods of processing and utilizing the xylose mother liquor is focused on an extraction of the xylose and the arabinose in the xylose mother liquor. For example, bacteria or yeast are used to ferment the xylose mother liquor to reduce a difficulty of extraction and separation. When the glucose or galactose in the xylose mother liquor are consumed out as a carbon source for the growth of the bacteria, an efficiency of extracting the xylose and the arabinose is improved. The above fermentation process for removing the glucose or the galactose has some limitations. For example, a high sugar content in xylose mother liquor is generally unsuitable for the bacterial to grow, an osmotolerant yeast are mostly used in an aerobic fermentation, which needs for large compressed air. The xylose mother liquor needs to be diluted, and a mother liquor after dilution has a large liquid volume. A utilization of all glucose in the mother liquor requires a larger amount of cells, and culture for multiple times. The fermentation time may be 48 hours or even longer. Although the purpose of purifying the xylose and the arabinose can be achieved through the above process, the energy consumption, production cycle and cost increase significantly.

Therefore, it is desirable to provide a method for co-producing the erythritol and the arabinose by utilizing the xylose mother liquor to improve a utilization rate and a utilization value of the xylose mother liquor and reduce utilization costs.

SUMMARY

According to one or more embodiments of the present disclosure, a method for the co-producing erythritol and arabinose by utilizing a xylose mother liquor is provided, including:

obtaining a xylose extract having a high content of xylose component and a xylose raffinate having a high content of glucose component respectively by separating the xylose mother liquor through a first simulated moving bed chromatography, and obtaining xylose crystals by concentrating and crystallizing the xylose extract;

obtaining a concentrated xylose raffinate by concentrating the xylose raffinate, and obtaining a glucose mixture by blending the concentrated xylose raffinate with liquid glucose or crystallized glucose, wherein the concentrated xylose raffinate has a solid content of 30% W/V~50% W/V and a glucose content of 9% W/V~14% W/V, the glucose mixture has a glucose content of 40% W/V~50% W/V;

obtaining a fermentation broth by inoculating a pre-prepared seed solution of a *Yarrowia lipolytica* into a fermentation medium of a fermenter, while adding a glucose mixture for fermenting, wherein the glucose content of the fermentation broth is <0.3% W/V;

obtaining a fermentation filtrate by filtering the fermentation broth, and respectively obtaining erythritol crystals and a centrifuged erythritol mother liquor by decolorizing, ion changing, concentrating, centrifuging and crystallizing the fermentation filtrate in sequence;

obtaining an erythritol extract having a high content of an erythritol component and an erythritol raffinate having a high content of an arabinose component respectively by separating the centrifuged erythritol mother liquor through a second simulated moving bed chromatography, and mixing the erythritol extract with the fermentation filtrate; and obtaining arabinose crystals by decolorizing, ion changing, concentrating and crystallizing the erythritol raffinate in sequence.

In some embodiments, the fermentation medium is prepared by glucose 5% W/V~32% W/V of glucose, 0.5% W/V~1% W/V of yeast paste, 0.3% W/V~0.8% W/V of corn pulp dry powder, 0.03% W/V~0.08% W/V of magnesium sulfate, 0.2% W/V~0.8% W/V of ammonium citrate and 0.02% W/V~0.05% W/V of dipotassium hydrogen phosphate.

In some embodiments, the pre-prepared seed solution of the *Yarrowia lipolytica* is prepared according to the following operations: inoculating a *Yarrowia lipolytica* strain into the slant test tube seed medium for cultivation to obtain a slant test tube seed culture, wherein the slant test tube seed medium is prepared by: 0% W/V~25% W/V of glucose, 0.8% W/V~1.5% W/V of yeast paste and 1.5% W/V~2% W/V of agar. The pre-prepared seed solution of the *Yarrowia lipolytica* is prepared by using the slant test tube seed culture.

In some embodiments, he pre-prepared seed solution of the *Yarrowia lipolytica* is prepared according to the following operations: inoculating a *Yarrowia lipolytica* strain into a slant eggplant-type flask seed medium for cultivation to obtain a slant eggplant-type flask seed culture, wherein the slant eggplant-type flask seed medium is prepared by: 20% W/V~25% W/V of glucose, 0.8% W/V~1.5% W/V of yeast paste and 1.5% W/V~2% W/V of agar. The pre-prepared seed solution of the *Yarrowia lipolytica* is prepared by using the slant eggplant-type flask seed culture.

In some embodiments, the pre-prepared seed solution of the *Yarrowia lipolytica* is prepared according to the following operations: inoculating a *Yarrowia lipolytica* strain into a shake flask for cultivation to obtain a shake flask seed solution, wherein the slant shake flask seed medium is prepared by: 20% W/V~25% W/V of glucose, 0.8%

W/V~1.5% W/V of yeast paste, 0.03% W/V~0.08% W/V of magnesium sulfate and 0.2% W/V~0.7% W/V of ammonium citrate. The pre-prepared seed solution of the *Yarrowia lipolytica* is prepared by using the shake flask seed solution.

In some embodiments, the pre-prepared seed solution of the *Yarrowia lipolytica* is prepared according to the following operations: inoculating a *Yarrowia lipolytica* strain into the fermenter seed medium for cultivation to obtain a fermenter seed solution, wherein the fermenter seed medium is prepared by: 25% W/V~30 30% W/V of glucose, 0.5% W/V~1.0% W/V of yeast paste, 0.3% W/V~0.8% W/V of peptone, 0.03% W/V~0.08% W/V of magnesium sulfate and 0.2% W/V~0.8% W/V of ammonium citrate, 5% W/V~10% W/V of an amount of inoculum, 6.0~7.0 of an initial pH of fermentation, 115° C.~121° C. of a sterilization temperature of the fermenter seed medium, 20 min~30 min of sterilization time. The pre-prepared seed solution of the *Yarrowia lipolytica* is prepared by using the fermenter seed solution.

Based on the method of the embodiments of the present disclosure, arabinose and erythritol can be co-produced by utilizing the xylose mother liquor, which may realize an efficient utilization of the xylose mother liquor, and may reduce fermentation costs, improve the added value of the xylose mother liquor, and increase economic benefits. In particular, during a process of fermenting and producing the erythritol, the glucose mixture is produced by blending the xylose raffinate with the glucose (i.e., mixing liquid glucose or crystallized glucose). On the one hand, increase the glucose content in the fermentation medium, thereby increasing the yield of the erythritol in each batch of the fermentation broth, and on the other hand, increase the utilization rate of each batch of the xylose raffinate during fermentation. When the erythritol is prepared by blending the xylose raffinate with the glucose for fermentation, a concentration of the erythritol is larger than 156 g/L and a conversion rate is larger than 52%.

BRIEF DESCRIPTION OF THE DRAWINGS

The present disclosure will be further illustrated by way of exemplary embodiments, which will be described in detail by way of the accompanying drawings. These embodiments are not limiting, and in these embodiments, the same counting indicates the same structure, wherein:

FIG. 1 illustrates a flow chart illustrating an exemplary method for co-producing erythritol and arabinose by utilizing a xylose mother liquor of the present disclosure.

DETAILED DESCRIPTION

To more clearly illustrate the technical solutions of the embodiments of the present disclosure, the accompanying drawings that need to be used in the description of the embodiments would be briefly introduced below. Obviously, the accompanying drawing in the following description is merely some examples or embodiments of the present disclosure, and those skilled in the art can apply the present disclosure to other similar situations according to the drawings without any creative effort. Unless obviously obtained from the context or the context illustrates otherwise, the same numeral in the drawings indicates the same structure or operation.

As used in the present disclosure and the appended claims, the singular forms "a," "an," and "the" are intended to include plural referents, unless the content clearly dictates otherwise. Generally, the terms "comprise" and "include" only imply that the clearly identified steps, elements and/or materials are included, but these steps, elements and/or materials do not constitute an exclusive list, and the method or platform may further include other steps, elements and/or materials.

Unless otherwise defined, all technical and scientific terms used herein have the same meaning as commonly understood by one of ordinary skill in the art to which this disclosure belongs.

Some embodiments of the present disclosure provide a method for co-producing erythritol and arabinose by utilizing a xylose mother liquor. The method includes the following operations.

In step (a), a xylose raffinate enriched with a glucose component is obtained by separating the xylose mother liquor.

In some embodiments, the xylose mother liquor includes a xylose component, the glucose component, and other sugar components (e.g., an arabinose, a galactose, etc.). A separation of the xylose mother liquor refers to separating the xylose component from the xylose mother liquor and obtain the xylose raffinate.

The term "enriched" refers to an increase in the proportion of a target component relative to a non-target component. In some embodiments, after the separation, the xylose raffinate is enriched with the glucose component relative to the xylose component. In some embodiments, after separation, the xylose raffinate has an increased proportion of arabinose component relative to the xylose component.

In some embodiments, a xylose extract enriched with the xylose component is further obtained through the separation of the xylose mother liquor. After separation, the xylose extract has an increased proportion of the xylose component relative to the glucose component and/or other sugar components. The xylose extract may be used, for example, to continue to prepare xylose crystals. In some embodiments, the method further includes the operation of obtaining the xylose crystals by concentrating and crystallizing the xylose extract.

In some embodiments, the separation of the xylose mother liquor may be performed by membrane separation technology, such as ultrafiltration (UF), microfiltration (MF), or nanofiltration (NF). In some embodiments, the separation of the xylose mother liquor may be performed by chromatographic separation technology, such as gel filtration chromatography (GFC), ion exchange chromatography (IEC), simulated moving bed chromatography (SMB), gel permeation chromatography (GPC), high performance liquid chromatography (HPLC), or gas chromatography (GC), etc. In some embodiments, the separation of the xylose mother liquor is performed by SMB.

In step (b), a glucose mixture is obtained by concentrating the xylose raffinate and glucose blending process.

In some embodiments, a concentration of the xylose raffinate may increase a glucose content of the xylose raffinate, thereby increasing the glucose content in the fermentation medium. A suitable content of each component makes a concentrated xylose raffinate suitable for fermenting erythritol. In some embodiments, in the concentrated xylose raffinate, the content of the solids is within a range of 30% W/V~50% W/V of solids, such as 30% W/V, 35% W/V, 40% W/V, 45% W/V, or 50% W/V. In some embodiments, in the concentrated xylose raffinate, the content of the glucose is within a range of 9% W/V~14% W/V, such as 9% W/V, 10% W/V, 11% W/V, 12% W/V, 13% W/V or 14% W/V. It should be noted that the symbol "% W/V" in the present disclosure indicates weight/volume percentage (g/100 mL).

In some embodiments, a glucose blending process of the xylose raffinate may further increase the glucose content in the fermentation medium to provide an adequate and good carbon source for the fermentation of the erythritol and to increase yield of the erythritol. In some embodiments, the glucose used for the blending may be liquid glucose and/or crystallized glucose, and the glucose mixture may be obtained by blending the concentrated xylose extract with the liquid glucose and/or the crystallized glucose.

In some embodiments, a suitable glucose content in the glucose mixture may ensure a utilization rate of the glucose as the carbon source in the fermentation for erythritol. In some embodiments, in the glucose mixture, the glucose content is within a range of 40% W/V~50% W/V, such as 40% W/V, 41% W/V, 42% W/V, 43% W/V, 44% W/V, 45% W/V, 46% W/V, 47% W/V, 48% W/V, 49% W/V, or 50% W/V.

In step (c), a fermentation broth is obtained by adding the glucose mixture into a pre-prepared fermentation medium to which a seed solution of *Yarrowia lipolytica* is inoculated.

In some embodiments, the fermentation medium contains 25% W/V~32% W/V of glucose, 0.5% W/V~1% W/V of yeast paste, 0.3% W/V~0.8% W/V of corn pulp dry powder, 0.03% W/V~0.08% W/V of magnesium sulfate, 0.2% W/V~0.8% W/V of ammonium citrate and 0.02% W/V~0.05% W/V of dipotassium hydrogen phosphate. Exemplarily, the fermentation medium may contain the glucose of 25% W/V, 26% W/V, 27% W/V, 28% W/V, 29% W/V, 30% W/V, 31% W/V, or 32% W/V. The fermentation medium may contain the yeast paste of 0.5% W/V, 0.6% W/V, 0.7% W/V, 0.8% W/V, 0.9% W/V, or 1% W/V. The fermentation medium may contain the corn pulp dry powder of 0.3% W/V, 0.4% W/V, 0.5% W/V, 0.6% W/V, 0.7% W/V, or 0.8% W/V. The fermentation medium may contain the magnesium sulfate of 0.03% W/V, 0.04% W/V, 0.05% W/V, 0.06% W/V, 0.07% W/V, or 0.08% W/V. The fermentation medium may contain the ammonium citrate of 0.2% W/V, 0.3% W/V, 0.4% W/V, 0.5% W/V, 0.6% W/V, 0.7% W/V, or 0.8% W/V. The fermentation medium may contain the dipotassium hydrogen phosphate of 0.02% W/V, 0.03% W/V, 0.04% W/V, or 0.05% W/V. In some embodiments, the fermentation medium is prepared by blending the above components in corresponding proportions.

In some embodiments, the seed solution of the *Yarrowia lipolytica* is prepared by using the seed and/or the seed solution prepared by the operation selected from the group below: (i) a *Yarrowia lipolytica* strain is inoculated into a slant test tube seed medium for cultivation to obtain a slant test tube seed culture. (ii) The *Yarrowia lipolytica* strain is inoculated into a slant eggplant-type flask seed medium for cultivation to obtain a slant eggplant-type flask seed culture. (iii) The *Yarrowia lipolytica* strain is inoculated into a shake flask for cultivation to obtain a shake flask seed culture. (iv) The *Yarrowia lipolytica* strain is inoculated into the fermenter seed medium for cultivation to obtain a fermenter seed culture.

In some embodiments, an approach of preparing the seed solution of the *Yarrowia lipolytica* by using the seed and/or the seed solution described above may be determined based on a specific fermentation volume. In one specific example, at least one of the slant test tube seed culture, the slant eggplant-type flask seed culture, the shake flask seed culture, and the fermenter seed culture may be used directly as the seed solution of the *Yarrowia lipolytica*. In another specific example, at least one of the slant test tube seed culture, the slant eggplant-type flask seed culture, the shake flask seed culture, and the fermenter seed solution may be used in an expanded cultivation to obtain the seed solution of the *Yarrowia lipolytica*.

In some embodiments, the slant test tube seed medium and/or slant eggplant-type flask seed medium contains the glucose within a range of 20% W/V~25% W/V, the yeast paste within a range of 0.8% W/V~1.5% W/V, and the agar within a range of 1.5% W/V~2% W/V. Exemplarily, the slant test tube seed medium and/or slant eggplant-type flask seed medium may contain the glucose of 20% W/V, 21% W/V, 22% W/V, 23% W/V, 24% W/V, or 25% W/V of glucose. The slant test tube seed medium and/or slant eggplant-type flask seed medium may contain the yeast paste of 0.8% W/V, 0.9% W/V, 1% W/V, 1.1% W/V, 1.1% W/V, or 25% W/V. The slant test tube seed medium and/or slant eggplant-type flask seed medium may contain the agar of 1.5% W/V, 1.6% W/V, 1.7% W/V, 1.8% W/V, 1.9% W/V, or 2% W/V.

In some embodiments, the shake flask seed medium contains the glucose within a range of 20% W/V~25% W/V, the yeast paste within a range of 0.8% W/V~1.5% W/V, the magnesium sulfate within a range of 0.03% W/V~0.08% W/V, and the ammonium citrate within a range 0.2% W/V~0.7% W/V. Exemplarily, the shake flask seed medium may contain the glucose of 20% W/V, 21% W/V, 22% W/V, 23% W/V, 24% W/V, or 25% W/V. The shake flask seed medium may contain the yeast paste of 0.8% W/V, 0.9% W/V, 1% W/V, 1.1% W/V, 1.2% W/V, 1.3% W/V, 1.4% W/V, or 1.5% W/V. The shake flask seed medium may contain the magnesium sulfate of 0.03% W/V, 0.04% W/V, 0.05% W/V, 0.06% W/V, 0.07% W/V, or 0.08% W/V. The shake flask seed medium may contain the ammonium citrate of 0.2% W/V, 0.3% W/V, 0.4% W/V, 0.5% W/V, 0.6% W/V, or 0.7% W/V.

In some embodiments, the fermenter seed medium includes the glucose within a range of 25% W/V~30% W/V, the yeast paste within a range 0.5% W/V~1.0% W/V, peptone within a range of 0.3% W/V~0.8% W/V, the magnesium sulfate within a range of 0.03% W/V~0.08% W/V, and the ammonium citrate 0.2% W/V within a range of W/V~0.8% W/V. Exemplary, the fermenter seed medium may contain the glucose of 25% W/V, 26% W/V, 27% W/V, 28% W/V, 29% W/V or 30% W/V. The fermenter seed medium may contain the yeast paste of 0.5% W/V, 0.6% W/V, 0.7% W/V, 0.8% W/V, 0.9% W/V or 1% W/V. The fermenter seed medium may contain the peptone of 0.3% W/V, 0.4% W/V, 0.5% W/V, 0.6% W/V, 0.7% W/V or 0.8% W/V. The fermenter seed medium may contain the magnesium sulfate of 0.03% W/V, 0.04% W/V, 0.05% W/V, 0.06% W/V, 0.07% W/V or 0.08% W/V. The fermenter seed medium may contain the ammonium citrate of 0.2% W/V, 0.3% W/V, 0.4% W/V, 0.5% W/V, 0.6% W/V W/V, 0.7% W/V, or 0.8% W/V.

In some embodiments, culture conditions for inoculating a *Yarrowia lipolytica* strain into the fermenter for cultivation includes: an inoculum quantity of the *Yarrowia lipolytica* strain is within a range of 5% W/V~10% W/V. An initial pH of fermentation is within a range of 6.0~7.0. A sterilization temperature of the fermenter seed medium is within a range of 115° C.~121° C., and sterilization time is within a range of 20 min~30 min.

In some embodiments, the *Yarrowia lipolytica* may efficiently utilize the glucose in the fermentation medium and convert the glucose into the erythritol. In some embodiments, the glucose content of the fermentation broth is <0.3% W/V.

In step (d), erythritol crystals and a centrifuged erythritol mother liquor are obtained by filtering, separating and purifying the fermentation broth.

In some embodiments, step (d) further includes: obtaining the fermentation broth by filtering the fermentation broth; and obtaining the erythritol crystals and centrifuged erythritol mother liquor by decolorizing, dissociating, concentrating, centrifuging and crystallizing a portion of the fermentation filtrate.

The term "decolorization" refers to a removal of pigmented substances. In some embodiments, the decolorization may be done by adsorbing to remove the pigmented substances, such as absorbing by activated carbon or microporous resin. In some embodiments, the decolorization may be done by degrading to remove the pigmented substances, such as degrading by hydrogen peroxide.

The term "ion exchange" refers to a utilization of ion exchange technology to remove non-sugar substances, such as soluble salts.

In step (e), an erythritol raffinate enriched with the arabinose component is obtained by separating a centrifuged erythritol mother liquor.

In some embodiments, the centrifuged erythritol mother liquor includes an erythritol component and an arabinose component. The separation of the centrifuged erythritol mother liquor is configured to separate the erythritol component from the centrifuged erythritol mother liquor, and obtain an erythritol raffinate. In some embodiments, after separation, a proportion of the arabinose component is increased in the erythritol raffinate relative to the erythritol component.

In some embodiments, an erythritol extract enriched with the erythritol component is further obtained by separating the erythritol centrifuged mother liquor. After separation, the proportion of the erythritol component of the erythritol extract is increased relative to the arabinose component. In some embodiments, the method further includes: mixing the erythritol extract with another portion of the fermentation filtrate. The mixture of the erythritol extract and the fermentation filtrate may be used, for example, to continue to prepare the erythritol crystals.

In some embodiments, the separation of the centrifuged erythritol mother liquor may be performed through the membrane separation technology, such as the ultrafiltration (UF), the microfiltration (MF), or the nanofiltration (NF). In some embodiments, the separation of the centrifuged erythritol mother liquor may be performed through the chromatographic separation technology, such as the gel filtration chromatography (GFC), the ion exchange chromatography (IEC), the simulated moving bed chromatography (SMB), the gel permeation chromatography (GPC), the high performance liquid chromatography (HPLC), or the gas chromatography (GC), etc. In some preferred embodiments, the separation of the centrifuged erythritol mother liquor is performed through SMB.

In step (f), the arabinose crystals are obtained by separating and purifying the erythritol raffinate.

In some embodiments, the separation and purification of the erythritol raffinate includes decolorization, ion exchange, concentration and crystallization in sequence.

The method for co-producing the erythritol and the arabinose by utilizing the xylose mother liquor provided by some embodiments performs a first separation by using the xylose mother liquor to obtain the xylose raffinate enriched with the glucose component. The xylose raffinate is blended with the glucose and then the *Yarrowia lipolytica* with high osmotolerant and a high conversion rate is fermented to produce the erythritol. According to the method, the erythritol mother liquor is obtained by separating and purifying the erythritol crystals from the fermentation broth utilizing characteristics of low solubility degree and easy crystallization of the erythritol. According to the method, an efficient utilization of the xylose mother liquor may be achieved, the fermentation costs may be reduced, the added value of xylose mother liquor may be increased, and the economic benefits may be improved.

FIG. 1 is an exemplary flow diagram of a method for co-producing erythritol and arabinose by utilizing xylose mother liquor according to some embodiments of the present disclosure. In some embodiments, as shown in FIG. 1, a flow of co-producing the erythritol and the arabinose by utilizing the xylose mother liquor includes obtaining the xylose extract having the high content of the xylose component and the xylose raffinate having the high content of glucose component by separating the xylose mother liquor through a first simulated moving chromatography separation (e.g., SMB), and obtaining xylose crystals by concentrating and crystallizing the xylose extract. The flow of co-producing the erythritol and the arabinose by utilizing the xylose mother liquor further includes obtaining a concentrated xylose raffinate by concentrating the xylose raffinate, and obtaining a glucose mixture by blending the concentrated xylose raffinate with the liquid glucose or the crystallized glucose. The flow of co-producing the erythritol and the arabinose by utilizing the xylose mother liquor further includes obtaining the fermentation broth by inoculating a pre-prepared seed solution of the *Yarrowia lipolytica* into a fermentation medium of the fermenter, while adding the glucose mixture for fermenting. The flow of co-producing the erythritol and the arabinose by utilizing the xylose mother liquor further includes obtaining the erythritol extract having the high content of the erythritol component and the erythritol raffinate having the high content of the arabinose component respectively by separating the centrifuged erythritol mother liquor through a second chromatography (e.g., SMB), and mixing the erythritol extract with another portion of the fermentation filtrate. The flow of co-producing the erythritol and the arabinose by utilizing the xylose mother liquor further includes obtaining the arabinose crystals by decolorizing, ion changing, concentrating and crystallizing the erythritol raffinate in sequence.

According to method for co-producing the erythritol and the arabinose by utilizing the xylose mother liquor provided by some embodiments in the present disclosure, the efficient utilization of xylose mother liquor may be achieved, the xylose and the arabinose may be obtained, meanwhile the erythritol may be produced by using the glucose of the xylose and the arabinose. The method described above may reduce the fermentation costs, increase the added value of the xylose mother liquor, and improve the economic benefits.

The following embodiments are some more specific descriptions of the embodiments related to some of the above embodiments. Partial descriptions of these embodiments may also be replaced or combined with corresponding descriptions of other embodiments to form new embodiments. The experimental methods in the following embodiments, unless otherwise specified, are all conventional methods. The test materials used in the following embodiments, if not otherwise specified, are purchased from conventional biochemical reagent companies. For the quantitative tests in the following embodiments, three replicate experiments were set up and the results were averaged. It should be understood that the following embodiments are intended to better explain the present disclosure and are not intended to limit the present disclosure.

Embodiment 1

The xylose mother liquor was separated by the first chromatography to obtain the xylose extract enriched with the xylose component and the xylose extract enriched with the glucose component. The extract was concentrated to have 80% W/V of solids, and crystallized xylose was obtained by evaporating crystallization. The proportion of each component in the xylose raffinate was 25% W/V~32% W/V of the glucose, 18% W/V~25% W/V of the arabinose, 5% W/V~15% W/V of the galactose. The raffinate was concentrated to have 40% W/V of the solids, where the glucose content was 12% W/V, and was mixed with the crystallized glucose to obtain a mixture, so that the glucose content of the mixture was 45% W/V. A feeding system was 100 L, and other additives of the fermentation medium other than the glucose were added proportionally to the fermentation medium for sterilization and set aside.

The xylose raffinate was concentrated to have 40% W/V of the solids, where the glucose content was 12% W/V. The concentrated xylose raffinate was mixed with the crystallized glucose to obtain a mixture, so that the glucose content of the mixture was 45% W/V, a feeding system of 1000 L was prepared. Other additives of the fermentation medium other than the glucose were added proportionally to the feeding system for sterilization and set aside. The formulas of fermentation medium are shown in Table 1.

TABLE 1

| Formulations of Fermentation Medium | |
| --- | --- |
| Ingredients | Ratio/(% W/V) |
| Glucose | 25~32 |
| Yeast paste | 0.5~1 |
| Corn syrup dry powder | 0.3~0.8 |
| Magnesium sulfate | 0.03~0.08 |
| Ammonium citrate | 0.2~0.8 |
| Dipotassium hydrogen phosphate | 0.02~0.05 |

The feeding system of 70 L with 3 batches, the fermentation medium was fed during the fermentation process, the specific operations were as followed:

An initial fermentation volume was 40 L, the medium was prepared according to the above formulation of the fermentation medium as shown in Table 1, an initial glucose content in the medium was 18% W/V. The medium was prepared for sterilization, and set aside.

The shake flask seed medium was pre-prepared in the shake flask, and was prepared by 20% W/V~25% W/V of the glucose, 0.8% W/V~1.5% W/V of the yeast paste, 0.03% W/V~0.08% W/V of the magnesium sulfate and 0.2% W/V~0.7% W/V of the ammonium citrate. The shake flask seed was obtained by inoculating the *Yarrowia* lipolytic strain into the shake flask for cultivation. Shake flasks of 500 mL and 5 L respectively with a filling liquid volume of 10% W/V of the total volume were used to prepare shake flask seed cultures. The shake flask seeds were cultured for 20 h~24 h. When bacteria density (an absorbance value of bacterial solution in a wavelength of 600 nm, also referred to as an OD value) in the shake flask of 5 L was 18~25, the strain was inoculated into the fermenter, a volume of inoculum was 8% W/V, a fermentation temperature was 30° C., a speed of rotation was 200 rpm~400 rpm, dissolved oxygen was 20% W/V~30% W/V, a volume of aeration was 1.5 Nm3/h. When the bacteria density in the fermentation broth reached 35~40, the above mixed sugar liquid was started to replenish to the fermenter to reach the volume to 70 L. During a continuous feeding process, a glucose content in the fermentation broth was kept at 17% W/V~20% W/V. After the feeding was completed, the fermentation was continued, when the glucose content in the fermentation broth was <0.3% W/V, the fermentation was stopped. The concentration of erythritol were all more than 156 g/L, and the conversion rate was ≥52.2% W/V.

TABLE 2

| Fermentation results | | | |
| --- | --- | --- | --- |
| | Batch I | Batch II | Batch III |
| Fermentation time/h | 102 | 97 | 100 |
| Concentration of Erythritol/(g/L) | 156.74 | 165.40 | 162.80 |
| Conversion rate/% W/V | 52.2 | 55.1 | 54.3 |

When the fermentation was ended, the fermentation broth was filtered through ceramic membrane to obtain supernatant, which was decolorized, ion changed and concentrated to have solids of 68% W/V. The solids then were cooled down and crystallized at a rate of 5° C./h, and after 20 h, erythritol crystals were obtained by centrifugation. The erythritol component and the arabinose component were obtained by separating the centrifuged mother liquor through the second simulated moving bed chromatography, the erythritol component was returned to a filtration supernatant to increase production of the erythritol. A purity of the arabinose reached 75% W/V, and the arabinose crystals were obtained by concentration, crystallization, and centrifugation.

Embodiment 2

The xylose extract enriched with the xylose component and the xylose raffinate enriched with the glucose component was obtained by separating the xylose mother liquor through first simulated moving bed chromatography. The obtaining of the raffinate and the proportion of each component were the same as in embodiment 1.

The raffinate was concentrated to have 50% W/V of solids, where the glucose content was 14.3% W/V, and liquid glucose was concentrated to have 65% W/V of the glucose content, and the concentrated xylose extract and the concentrated liquid glucose were mixed to obtain the mixture in a ratio of 4:6 by volume, so that the glucose content of the mixture was 45% W/V, a feeding system of 1000 L was prepared. Other additives of the fermentation medium other than the glucose were added proportionally to the formulations of the fermentation medium as shown in Table 1 for sterilization and set aside.

The feeding system of 70 L with 3 batches, the fermentation medium was fed during the fermentation process, the specific operations were as followed:

The initial volume of fermentation was 400 L. The medium was prepared according to the formula shown in Table 1, with an initial glucose content of 18.7% W/V. The medium was sterilized after preparation and transferred to the fermenter to set aside.

The slant test tube seed medium was pre-prepared in the test tube, and was prepared by 20% W/V~25% W/V of the glucose, 0.8% W/V~1.5% W/V of the yeast paste, and 1.5%

W/V~2% W/V of the agar. The slant test tube seeds were obtained by inoculating the Yarrowia lipolytica strain into the slant test tube for cultivation. The slant test tube seeds were inoculated into slant eggplant-type flasks of 500 mL to prepare slant test tube seed cultures, and the slant test tube seeds were cultured in a temperature of 30° C. for 4~5 days. 80 mL of sterile water was added to each flask to wash down lawn. The lawn was respectively inoculated into the shake flasks of 5 L for being cultured for 20 h~24 h in a temperature of 30° C. When the bacteria density of the shake flask of 5 L was 18~25, the strain was inoculated into two seed fermenters of 50 L, where a filling liquid volume was 35 L, a temperature of the fermentation was 30° C., a pressure of the fermenter was 0.1 MPa. When the bacteria density reached 20~25, the strain in one seed fermenter was inoculated into a fermenter of 1000 ml for fermentation, where a rotation speed was 180 rpm~300 rpm, dissolved oxygen was 20% W/V 30% W/V, an aeration volume was 16 Nm$^3$/h. When the bacteria density reached 35~40, the above feeding system of 300 L was start to replenish to the seed fermenter, and meanwhile a new seed solution from another seed fermenter was added to the seed fermenter. During a continuous feeding process, a glucose content in the fermentation broth was kept at 17% W/V~20% W/V. After the feeding was completed, the fermentation was continued, when the glucose content in the fermentation broth was <0.3% W/V, the fermentation was stopped, a total concentration of the glucose of the feeding system was 30% W/V. The fermentation results are shown in Table 3, the concentration of erythritol were all more than 160 g/L, and the conversion rate was >53.9% W/V.

TABLE 3

Fermentation results

| | Batch I | Batch II | Batch III |
|---|---|---|---|
| Fermentation time/h | 104.5 | 101 | 106.5 |
| Concentration of erythritol/(g/L) | 160.71 | 165.40 | 162.80 |
| Conversion rate/% W/V | 53.9 | 55.5 | 54.6 |

When the fermentation was ended, the fermentation broth was filtered through the ceramic membrane to obtain the supernatant, which was decolorized, ion changed and concentrated to have solids of 65% W/V. The solids then were cooled down and crystallized at a rate of 6° C./h, and after 16 h, the erythritol crystals were obtained by centrifugation. The erythritol component and the arabinose component were obtained by separating the centrifuged mother liquor through the second simulated moving bed chromatography. The erythritol component was returned to the filtration supernatant, and the yield of the erythritol was increased. A purity of the arabinose component in the erythritol raffinate reached 77% W/V, and the arabinose crystals were obtained by concentration, crystallization, and centrifugation.

Embodiment 3

The xylose extract enriched with the xylose component and the xylose raffinate enriched with the glucose component was obtained by separating the xylose mother liquor through first simulated moving bed chromatography. The obtaining of the xylose raffinate and the proportion of each component were the same as in the embodiment 1 and the embodiment 2.

The raffinate was concentrated to have 48% W/V of solids, where the glucose content was 13.7% W/V. 550 L of water and 380 kg of crystalline dextrose monohydrate and tap water then were added to the solids to obtain the mixture, the glucose content of the mixture was 42% W/V, and the feeding system of 1000 L was prepared. Other additives of the fermentation medium other than the glucose were added proportionally to the formulations of the fermentation medium as shown in Table 1 for sterilization and set aside.

The fermentation system of 700 L with 3 batches, the fermentation medium was fed during the fermentation process, the specific operations were as followed:

An initial fermentation volume of 400 L, the medium was prepared according to the formulation of the medium shown in Table 1, an initial glucose content in the medium was 20% W/V. The medium was prepared for sterilization, and transferred to the fermenter to set aside.

A preparation of the slant test tube seeds was the same as in Example 2. The slant test tube seeds were inoculated into slant eggplant-type flask of 500 mL to prepare the slant test tube seed cultures, and the slant test tube seeds were cultured in the temperature of 30° C. for 4~5 days. 80 mL of sterile water was added to each flask to wash down the lawn. The lawn was respectively inoculated into the shake flask of 5 L for being cultured for 22 h in the temperature of 30° C. When the bacteria density was 18~25, the strain was inoculated into the two seed fermenters of 50 L, where the filling liquid volume was 35 L, the temperature of the fermentation was 30° C., the pressure of the fermenter was 0.1 MPa. When the bacteria density reached 20~25, the strain in one seed fermenter was inoculated into the fermenter of 1000 ml, where a rotation speed was 180 rpm~300 rpm, the dissolved oxygen was 20% W/V~30% W/V, an aeration volume was 15 Nm$^3$/h. When the bacteria density reached 35~40, the above feeding system of 300 L was start to replenish to the seed fermenter, and meanwhile a new seed solution from another seed fermenter was added to the seed fermenter. During a continuous feeding process, the glucose content in the fermentation broth was kept at 15% W/V~18% W/V. After the feeding was completed, the fermentation was continued, when the glucose content in the fermentation broth was <0.3% W/V, the fermentation was stopped, a total concentration of the glucose of the fermentation system was 30% W/V. The fermentation results are shown in Table 4, and the concentration of the erythritol in the fermentation broth were all more than 159 g/L, and the conversion rate ≥53.3% W/V.

TABLE 4

Fermentation results

| | Batch I | Batch II | Batch III |
|---|---|---|---|
| Fermentation time/h | 99.5 | 104 | 102.5 |
| concentration of erythritol/(g/L) | 163.57 | 159.80 | 165.22 |
| Conversion rate/% W/V | 54.5 | 53.3 | 55.1 |

When the fermentation was ended, the fermentation broth was filtered through the ceramic membrane to obtain the supernatant, which was decolorized, ion changed and concentrated to have solids of 67% W/V. The solids then were cooled down and crystallized at a rate of 6° C./h, and after 18 h, the erythritol crystals were obtained by centrifugation. The erythritol component and the arabinose component were obtained by separating the centrifuged mother liquor through the second simulated moving bed chromatography, the erythritol component was returned to the filtration supernatant. A purity of the arabinose component reached 78%

W/V, and the arabinose crystals were obtained by concentration, crystallization, and centrifugation.

Comparative Embodiment 1

The chromatographic raffinate having the solids of 30% W/V was configured for use as an initial fermentation medium for direct fermentation to prepare the erythritol. The initial glucose content of the fermentation medium was 7.2% W/V. Except for the feeding fermentation, a 70 L fermentation system and a fermentation control of the embodiment 1 were used. When the fermentation was ended, the concentration of the erythritol was 31.6 g/L, and the conversion rate was 43.8% W/V.

Comparative Embodiment 2

The chromatography raffinate having solids of 30-40% W/V are mixed with the crystallized glucose, the liquid glucose and the dextrose monohydrate to obtain the glucose mixture. The above glucose mixture was configured to be used as the initial fermentation medium to directly ferment and prepare the erythritol. The initial glucose content of the fermentation medium was 21% W/V. Except for the feeding fermentation process, the 70 L fermentation system and the fermentation control of the embodiment 1 are used. When the fermentation is ended, the concentration of the erythritol was 64.5 g/L, and a conversion rate was 30.0% W/V.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

At the same time, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of the present disclosure are not necessarily all referring to the same embodiment. Furthermore, the particular features, structures, or characteristics may be combined as suitable in one or more embodiments of the present disclosure.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% W/V variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for co-producing erythritol and arabinose by utilizing a xylose mother liquor, comprising:

obtaining a xylose extract having a high content of xylose component and a xylose raffinate having a high content of glucose component respectively by separating the xylose mother liquor through a first simulated moving bed chromatography, and obtaining xylose crystals by concentrating and crystallizing the xylose extract;

obtaining a concentrated xylose raffinate by concentrating the xylose raffinate, and obtaining a glucose mixture by blending the concentrated xylose raffinate with liquid glucose or crystallized glucose, wherein the concentrated xylose raffinate has a solid content of 30% W/V-50% W/V and a glucose content of 9% W/V-14% W/V, the glucose mixture has a glucose content of 40% W/V-50% W/V;

obtaining a fermentation broth by inoculating a pre-prepared seed solution of a *Yarrowia lipolytica* into a fermentation medium of a fermenter, while adding the glucose mixture for fermenting, wherein a glucose content of the fermentation broth is less than 0.3% W/V;

obtaining a fermentation filtrate by filtering the fermentation broth, and obtaining erythritol crystals and a centrifuged erythritol mother liquor respectively by decolorizing, ion changing, concentrating, centrifuging and crystallizing a part of the fermentation filtrate in sequence;

obtaining an erythritol extract having a high content of an erythritol component and an erythritol raffinate having a high content of an arabinose component respectively by separating the centrifuged erythritol mother liquor through a second simulated moving bed chromatography, and mixing the erythritol extract with the other part of the fermentation filtrate; and obtaining arabinose crystals by decolorizing, ion changing, concentrating and crystallizing the erythritol raffinate in sequence.

2. The method for co-producing the erythritol and the arabinose by utilizing the xylose mother liquor of claim 1, wherein the fermentation medium is prepared by 25% W/V-32% W/V of glucose, 0.5% W/V-1% W/V of yeast paste, 0.3% W/V-0.8% W/V of corn pulp dry powder, 0.03% W/V-0.08% W/V of magnesium sulfate, 0.2% W/V-0.8% W/V of ammonium citrate, and 0.02% W/V-0.05% W/V of dipotassium hydrogen phosphate.

3. The method for co-producing the erythritol and the arabinose by utilizing the xylose mother liquor of claim 1, wherein the pre-prepared seed solution of the *Yarrowia lipolytica* is prepared according to the following operations:
inoculating a *Yarrowia lipolytica* strain into a slant test tube seed medium for cultivation to obtain a slant test tube seed culture, wherein the slant test tube seed medium is prepared by: 20% W/V-25% W/V of glucose, 0.8% W/V-1.5% W/V of yeast paste and 1.5% W/V-2% W/V of agar; and
preparing the pre-prepared seed solution of the *Yarrowia lipolytica* by using the slant test tube seed culture.

4. The method for the co-producing the erythritol and the arabinose by utilizing the xylose mother liquor of claim 1, wherein the pre-prepared seed solution of the *Yarrowia lipolytica* is prepared according to the following operations:
inoculating a *Yarrowia lipolytica* strain into a slant eggplant-type flask seed medium for cultivation to obtain a slant eggplant-type flask seed culture, wherein the slant eggplant-type flask seed medium is prepared by: 20% W/V-25% W/V of glucose, 0.8% W/V-1.5% W/V of yeast paste and 1.5% W/V-2% W/V of agar; and
preparing the pre-prepared seed solution of the *Yarrowia lipolytica* by using the slant eggplant-type flask seed culture.

5. The method for the co-producing the erythritol and the arabinose by utilizing the xylose mother liquor of claim 1, wherein the pre-prepared seed solution of the *Yarrowia lipolytica* is prepared according to the following operations:
inoculating a *Yarrowia lipolytica* strain into a shake flask seed medium for cultivation to obtain a shake flask seed culture, wherein the shake flask seed culture is prepared by: 20% W/V-25% W/V of glucose, 0.8% W/V-1.5% W/V of yeast paste, 0.03% W/V-0.08% W/V of magnesium sulfate and 0.2% W/V-0.7% W/V of ammonium citrate; and
preparing the pre-prepared seed solution of the *Yarrowia lipolytica* by using the shake flask seed culture.

6. The method for the co-producing the erythritol and the arabinose by utilizing the xylose mother liquor of claim 1, wherein the pre-prepared seed solution of the *Yarrowia lipolytica* is prepared according to the following operations:
inoculating a *Yarrowia lipolytica* strain into a fermenter seed medium for cultivation to obtain a fermenter seed culture, wherein the fermenter seed medium is prepared by: 25% W/V-30% W/V of glucose, 0.5% W/V-1.0% W/V of yeast paste, 0.3% W/V-0.8% W/V of peptone, 0.03% W/V-0.08% W/V of magnesium sulfate and 0.2% W/V-0.8% W/V of ammonium citrate, an inoculation quantity is 5% W/V-10% W/V, an initial pH of fermentation is 6.0~7.0, a sterilization temperature of the fermenter seed medium is 115° C.~121° C., sterilization time is 20 min-30 min; and
preparing the pre-prepared seed solution of the *Yarrowia lipolytica* by using the fermenter seed culture.

\* \* \* \* \*